United States Patent [19]

Geiselman

[11] Patent Number: 4,906,432

[45] Date of Patent: Mar. 6, 1990

[54] LIQUID HANDLING

[75] Inventor: Theodore S. Geiselman, Groveland, Mass.

[73] Assignee: Fisher Scientific Company, Pittsburgh, Pa.

[21] Appl. No.: 74,942

[22] Filed: Jul. 17, 1987

[51] Int. Cl.[4] .............................................. G01N 35/06
[52] U.S. Cl. .................................... 422/63; 422/100; 422/72
[58] Field of Search .................... 422/63–67, 422/81, 100, 72, 73; 137/884, 597, 559; 251/331

[56] References Cited

U.S. PATENT DOCUMENTS

| | | | |
|---|---|---|---|
| 3,081,158 | 3/1963 | Winter | 422/100 |
| 4,298,571 | 11/1981 | DeFulvio | 422/64 |
| 4,304,257 | 12/1981 | Webster | 251/331 |
| 4,311,667 | 1/1982 | Gocho | 422/100 |
| 4,313,735 | 2/1982 | Yamashita et al. | 422/67 |
| 4,323,537 | 4/1982 | Mody | 422/81 |
| 4,341,736 | 7/1982 | Drbal et al. | 422/100 |
| 4,344,768 | 8/1982 | Parker et al. | 422/100 |
| 4,456,037 | 6/1984 | Gocho | 422/100 |
| 4,601,881 | 7/1986 | Webster | 422/68 |
| 4,670,219 | 6/1987 | Nelson et al. | 422/67 |
| 4,738,824 | 4/1988 | Takeuchi | 422/65 |
| 4,803,050 | 2/1989 | Mack | 422/65 |

Primary Examiner—Michael S. Marcus
Attorney, Agent, or Firm—Fish & Richardson

[57] ABSTRACT

An analysis system includes analysis station structure, sample station structure spaced from the analysis station structure along a straight line path, support shaft structure disposed along an axis parallel to the straight line path, and a transport carriage with probe structure mounted on the carriage. The transport carriage is mounted on the support shaft structure for movement along that shaft and is keyed thereto for pivoting movement in response to rotation of the shaft. A first drive includes a drive motor and cable structure coupled between the carriage and the drive motor for moving the transport carriage along the shaft to selectively position the probe structure at the sample and analysis stations, and a second drive rotates the shaft for inserting the probe into and withdrawing the probe from chamber structure at the sample and analysis stations. Metering means coupled to the probe flows liquid into and discharges liquid from the probe.

18 Claims, 3 Drawing Sheets

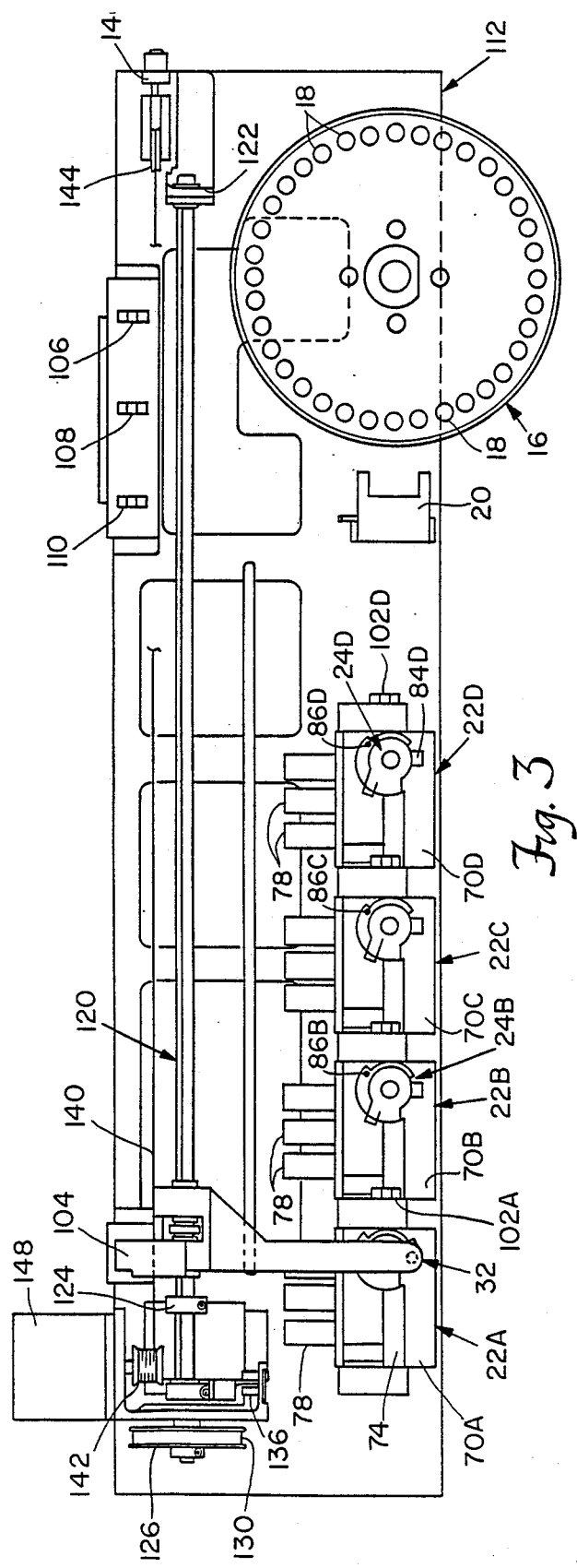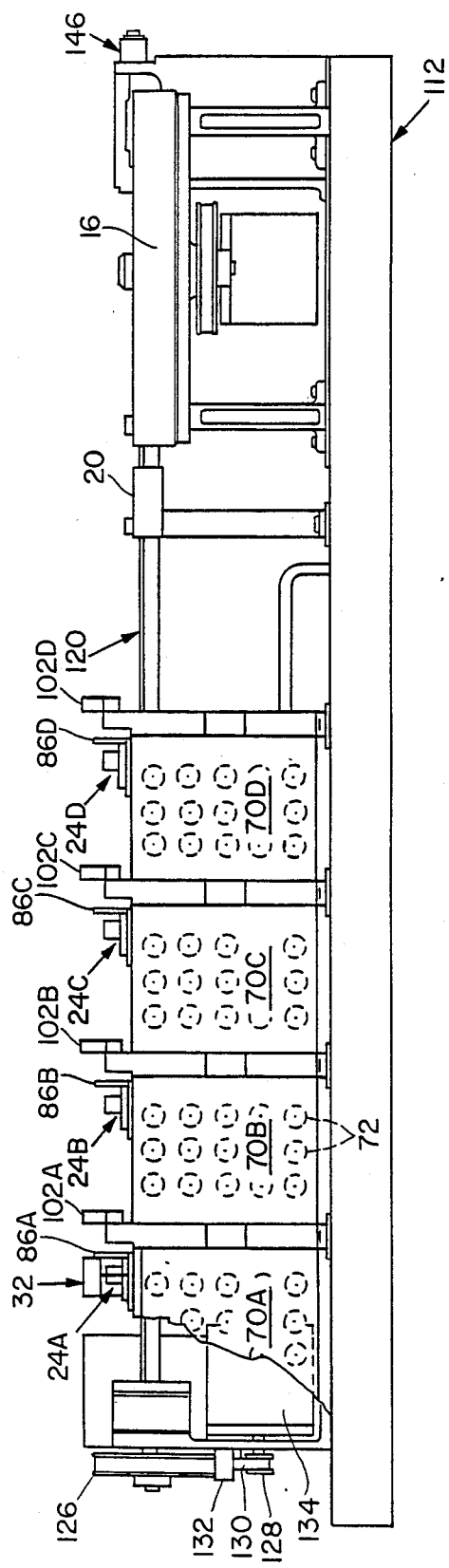

LIQUID HANDLING

This invention relates to liquid handling systems and has particular application to systems for the analysis of biological fluids and the like.

A variety of systems have been developed for the analysis of liquid samples. Frequently, in such systems, the sample to be analyzed is diluted or mixed with a reagent prior to analysis. In a multichannel system for the analysis of specific constituents of biological liquid samples such as whole blood, serum, plasma, or urine, required volumes of the sample liquid to be analyzed are mixed with prechosen reagents and/or diluents corresponding to one or more of the specific constituents of interest and disposed in corresponding analysis cells. A variety of arrangements for mixing sample and reagents or diluents and flowing the resulting mixtures to the analysis cells have been proposed. Liquid handling systems for such purposes are shown in Webster U.S. Pat. Nos. 4,304,275 and 4,601,881, for example. In analysis systems of the types shown in those patents, a modular unit with a valve array and interconnecting flow passages has inlet lines for sample and reagents, mixing chamber structure and an outlet line that is connected to the analysis cell or other utilization device. The fluids are flowed into and through the flow network module under the influence of reduced pressures from one or more reduced pressure manifolds which are selectively connected to the flow network by the integrated valve array.

In accordance with one aspect of the invention, there is provided an analysis system that includes analysis station structure, sample station structure spaced from the analysis station structure along a straight line path, support shaft structure disposed along an axis parallel to the straight line path, and a transport carriage with probe structure mounted on the carriage. The transport carriage is mounted on the support shaft structure for movement along that shaft structure and is keyed thereto for pivoting movement in response to rotation of the support shaft structure. First drive means includes a drive motor and cable structure coupled between the carriage and the drive motor for moving the transport carriage along the shaft to selectively position the probe structure at the sample and analysis stations, and second drive means rotates the shaft for inserting the probe structure into and withdrawing the probe structure from chamber structure at the sample and analysis station structures. Metering means coupled to the probe structure flows liquid into and discharges liquid from the probe structure.

In a particular embodiment, a plurality of flow network module structures are incorporated into a sample analysis system, each flow network module structure defining a contained array of flow channels and a plurality of valves for controlling liquid flow through the flow channel array, each module structure being adapted to be connected to an external source for applying a pressure differential to the flow channel array to produce liquid flow within channels of said array and each module structure having chamber structure connected to said flow channel array with port structure at an outer surface of said module structure. Valve structure is movable between a first position in which the port structure is closed and a second position in which the port structure is open. The system also includes a corresponding plurality of sensor modules. Liquid transfer structure is arranged for movement between a source of liquid to be analyzed and the plurality of flow network module structures and including valve actuator structure.

Preferably, the flow network module structure includes a face plate member that has a firm and stable support surface and a flexible sheet member that is clamped in conforming and mating engagement to the firm and stable face plate surface. A flow channel network is formed in the face plate member, together with valve land portions in one of the engaged surfaces that separates adjacent flow channel portions. Each valve also has an actuator which is arranged to flex the sheet member between a first position in which the surface of the valve sheet member is in mating and sealing engagement with the surface of the face plate member so that the valve land portion blocks flow between adjacent channel portions, and a second position in which the sheet surface is spaced from the first position and allows liquid flow across the land surface between the adjacent channel portions. Each valve has a small volume (less than ten microliters) when opened, and has essentially zero dead space when closed. The gentle and smooth closing action of the valve membrane is in a radially inward direction and the valves provide excellent isolation between the different liquids which are handled by the system.

In a particular embodiment, the sample chamber has a volume of about fifty microliters, the shaft is cylindrical and includes an axially extending groove in its surface, and the transport carriage includes bearing structure for engagement with the groove to allow axial motion of said transport carriage along the shaft and pivoting movement of the transport carriage in response to rotational movement of the shaft. The cable structure includes a drive sheave coupled to a drive motor, an idler sheave spaced from the drive sheave along a path parallel to the straight line path, and the cable is trained about the idler sheave, both ends of the cable being connected to the drive sheave. Biasing means for the idler sheave is arranged to apply tension to the cable.

Other features and advantages will be seen as the following description of a particular embodiment progresses, in conjunction with the drawings, in which:

FIG. 4 is a front view of the sample transfer system shown in FIG. 3;

DESCRIPTION OF PARTICULAR EMBODIMENT

Figure 1:
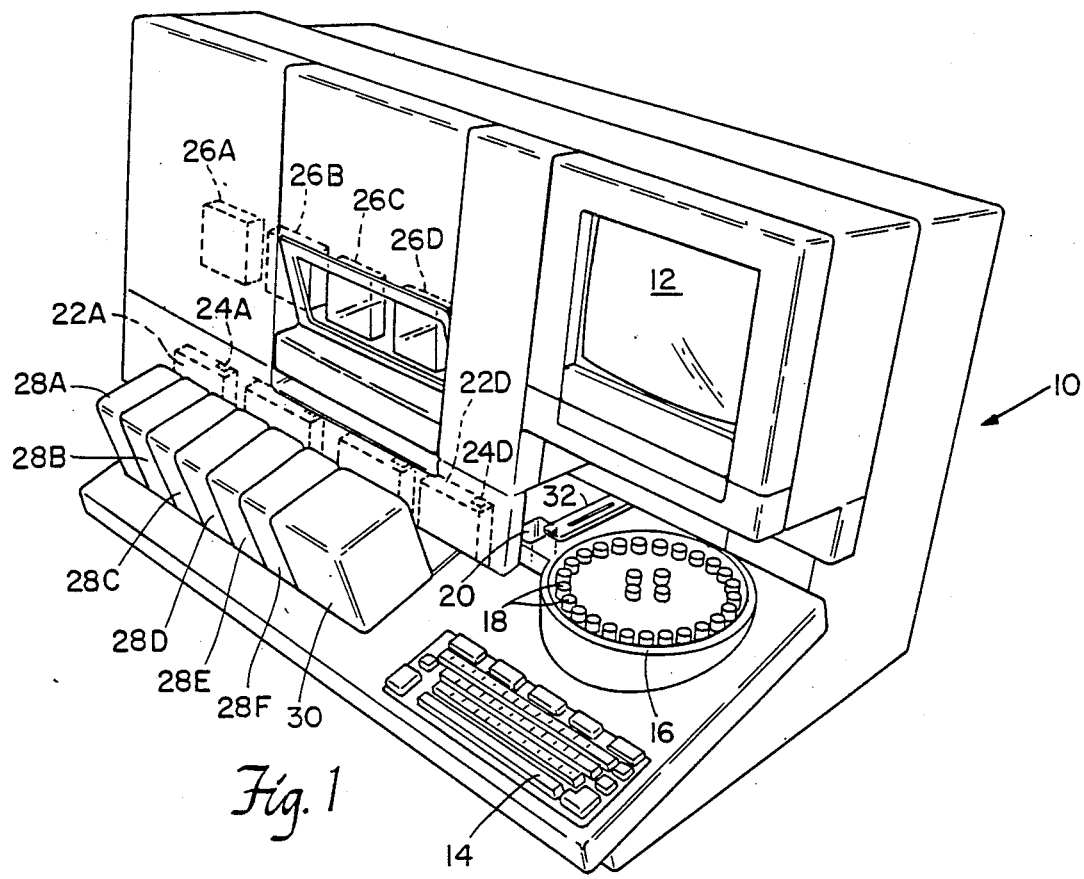
FIG. 1 is a perspective view of a clinical analyzer system in accordance with the invention.

Shown in FIG. 1 is a perspective view of a benchtop chemistry/electrolyte analyzer 10 that is arranged for measuring calcium, carbon dioxide, chloride, creatinine, glucose, potassium, sodium and urea nitrogen constituents of samples of biological fluids such as serum, urine and CFS. Analyzer 10 includes display 12, input keyboard 14, sample tray 16 that includes positions for forty sample cups 18 and four stat samples, wash station 20, four integrated fluidic modules 22A-D each with an inlet valve 24, four associated sensor modules 26A-D, six associated reagent containers 28A-F, and rinse liquid container 30. Sample liquids to be analyzed are transported by probe assembly 32 from containers 18 to fluidic modules 22.

Figure 2:
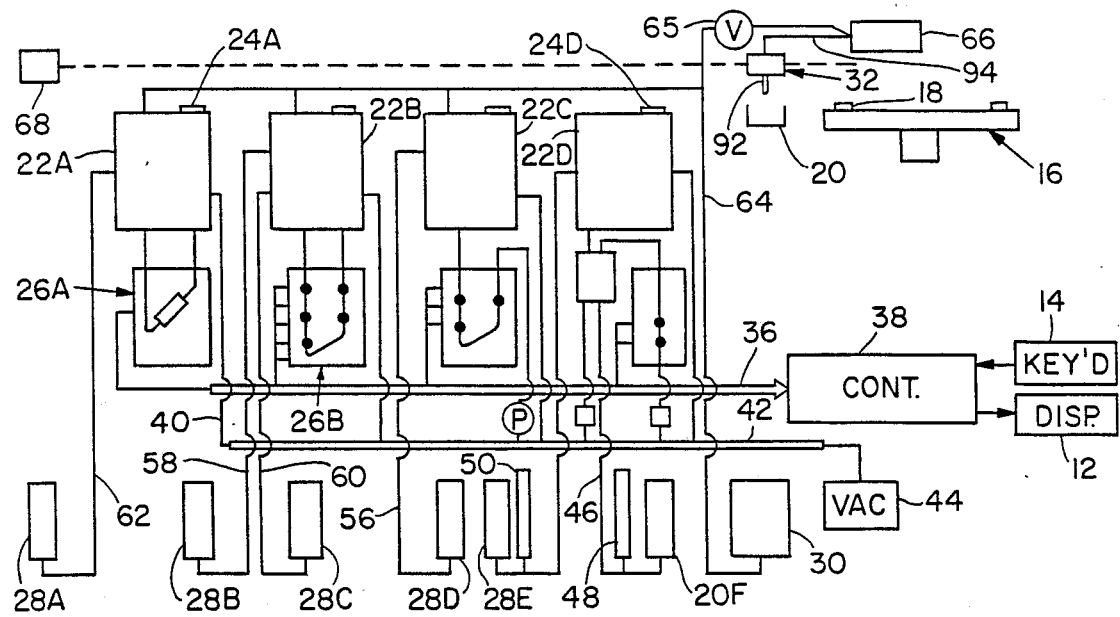
FIG. 2 is a block diagram of the analyzer system shown in FIG. 1.

Shown in FIG. 2 is a block diagram of the system shown in the FIG. 1. Fluidic module 22A is coupled to creatinine module 26A; fluidic module 22B is connected to ion selective electrode (calcium, chloride, potassium and sodium) module 26B; fluidic module 22C is connected to glucose urea nitrogen sensor module 26C (further details of that sensor system may be had with reference to copending application Ser. No. 074,882 entitled Sample Analysis filed concurrently herewith, the disclosure of which is specifically incorporated by reference) and fluidic module 22D is coupled through gas diffusion module 34 to carbon dioxide sensor module 26D, (further details of that system may be had with reference to copending application Ser. No. 075,052 entitled Analysis System filed concurrently herewith, the disclosure of which is also specifically incorporated herein by reference). Output signals from sensor modules 26 are applied over lines 36 to controller 38 for analysis and application to an output device such as display 12. Coupled to fluidic modules 22 by lines 40 is vacuum manifold 42 in which a vacuum of about nine inches of mercury is maintained by vacuum system 44. Connected to flow network module 22D by line 46 is positive displacement (syringe) pump 48 that supplies buffer reagent from source 28F over line 46; syringe pump 50 similarly supplies acid reagent from source 28E over line 52 to fluidic module 22D. Diluent reservoir 28D is connected over line 56 to fluidic module 22C; reservoirs 28B and 28C of ISE reference and buffer liquids are connected over lines 58 and 60 respectively to fluidic module 22B; and reservoir 28A of creatinine reagent is connected over line 62 to fluidic module 22A. Reservoir 30 of rinse liquid is connected by line 64 to fluidic modules 22A-22C and by valve 65 to syringe pump 66.

A quantity of sample to be analyzed is drawn by syringe pump 66 from sample cup 18 into probe assembly 32, and that probe assembly is translated by drive 68 between sample cup station 18, wash station 20 and the four valves 24A-24D of the fluidic modules 22A-22D. Each valve 24 seals a sample chamber port in the flow network module 22 and is moved to open position by probe assembly 32 so that a quantity sample to be analyzed may be inserted into the fluidic module 22 by operation of pump 66.

Figure 3:
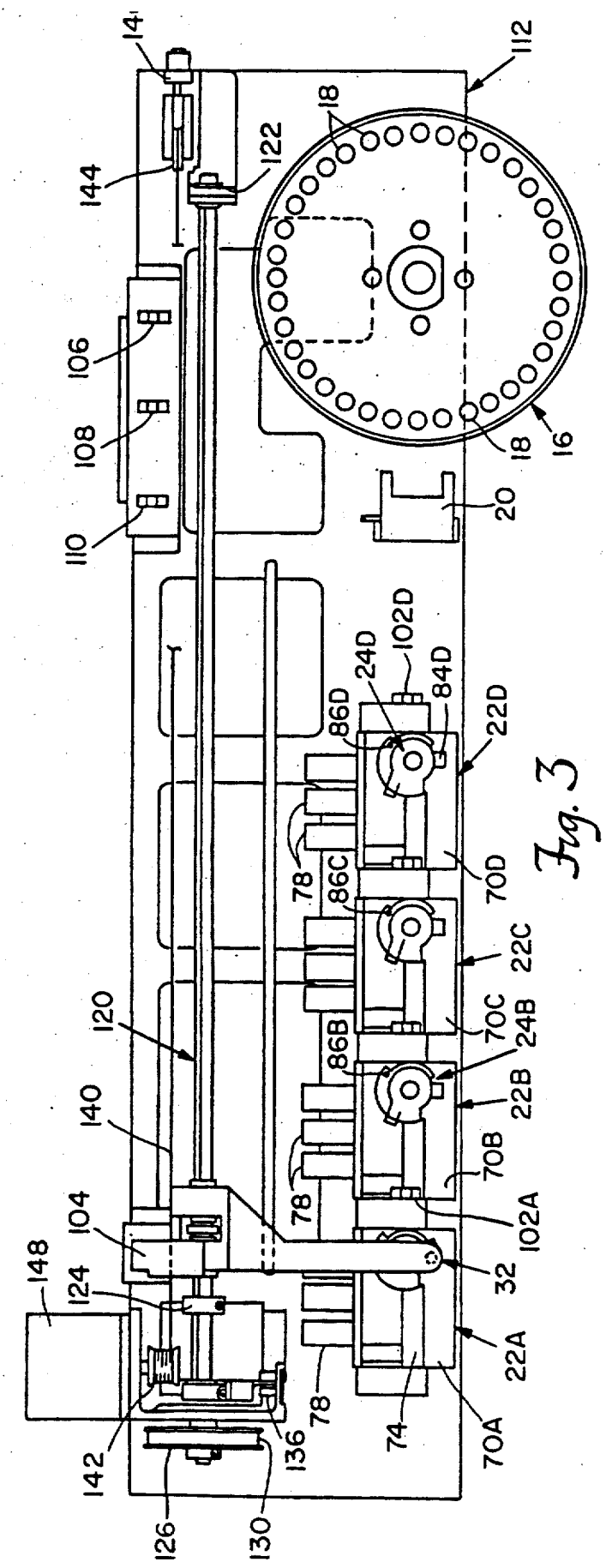
FIG. 3 is a top plan view showing the details of the sample transfer system employed in the analyzer system of FIG. 1.

Further details of the sample transport system may be seen with reference to FIGS. 3 and 4. Each flow network module 22 includes a rectangular faceplate 70 of acrylic resin in which a network of flow passages and valve sites 72 are formed, valve sites 72 being arranged in five rows and three columns and spaced about 1.5 centimeters on center. Clamped against the rear surface of faceplate 70 by backing plate 74 is valve diaphragm membrane sheet 76 (FIG. 7) to which is secured an array of valve actuator solenoids 78. Auxiliary fluid lines and reduced pressure lines are coupled to the modules 22 by connector tubes 80 (FIG. 7) that project from the front of faceplate 70. The fluidic modules 22 are of the type shown in Webster U.S. Pat. Nos. 4,304,257 and 4,601,881, the disclosures of which are specifically incorporated herein by reference.

Formed in the upper surface of each faceplate 70 is a sample introduction chamber 82 (FIG. 8) that is normally closed by valve member 84 that is operated by actuator post 86 of valve assembly 24 that is mounted on backing plate 74. Further details of that valve assembly may be had with reference to copending application Ser. No. 074,921, entitled Fluid Handling, filed concurrently herewith, the disclosure of which is specifically incorporated herein by reference.

Figure 7:
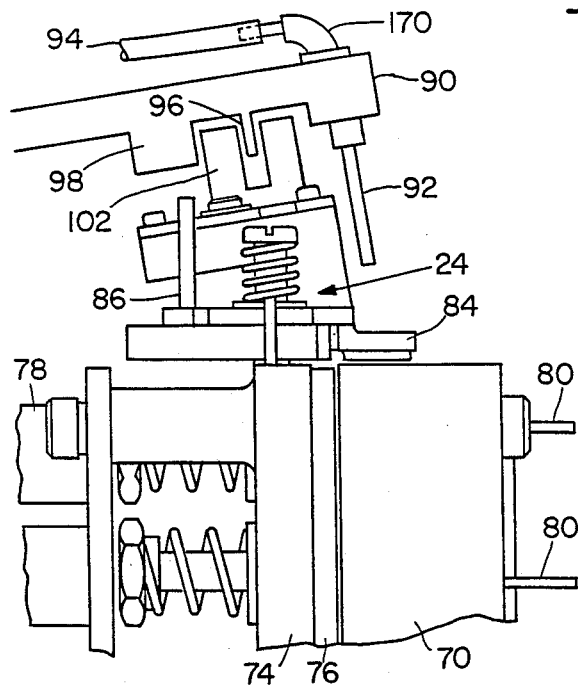
FIG. 7 is a side view proportion of the probe arm assembly and a cooperating fluidic module employed in the system shown in FIG. 1.
Figure 8:
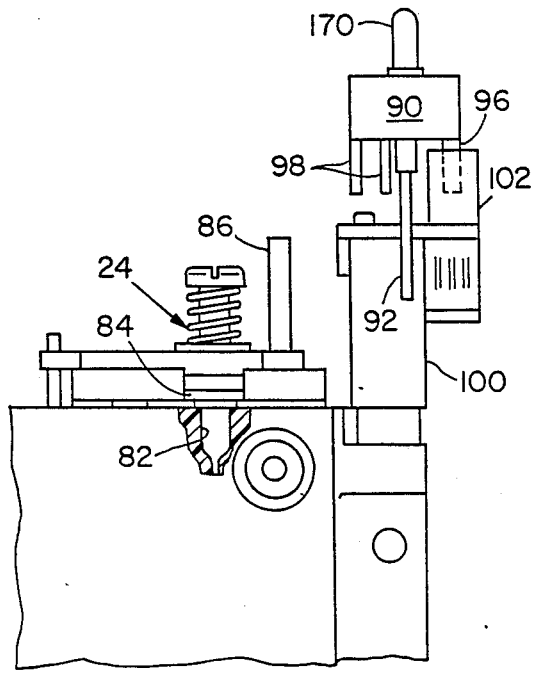
FIG. 8 is a front view of the components shown in FIG. 7.

The cooperating probe or transfer assembly 32 includes arm structure 90 that carries stainless steel probe 92 that is connected via tubing 94 to metering pump 66. Support arm 90 also includes depending sensor flag 96 and two spaced depending valve actuator members 98. Mounted on support 100 adjacent each fluidic module 22 is sensor assembly 102 that responds to the interposition of sensor flag 96, as indicated in FIGS. 7 and 8. Probe assembly 32 also includes sensor member 104 at the rear of the assembly 32 that cooperates with stat sensor 106, sample sensor 108, and wash sensor 110 mounted on the rear of support frame 112 (FIG. 3).

Probe arm assembly 32 is mounted on cylindrical shaft 120 that is supported for rotation by bearing assemblies 122, 124. Shaft 120 is connected by gears 126, 128 and drive timing belt 130 (that is maintained under tension by tensioning mechanism 132) to stepper drive motor 134. The angular position of shaft 120 is monitored by sensor assembly 136. Arm assembly 32 is coupled to steel stranded, nylon covered cable 140, both ends of which are attached to drive drum 142. Cable 140 extends to and is looped about idler sheave 144 that is biased by spring assembly 146 to maintain cable 140 under tension. Drive drum 142 is coupled to stepper motor 148.

Figure 5:
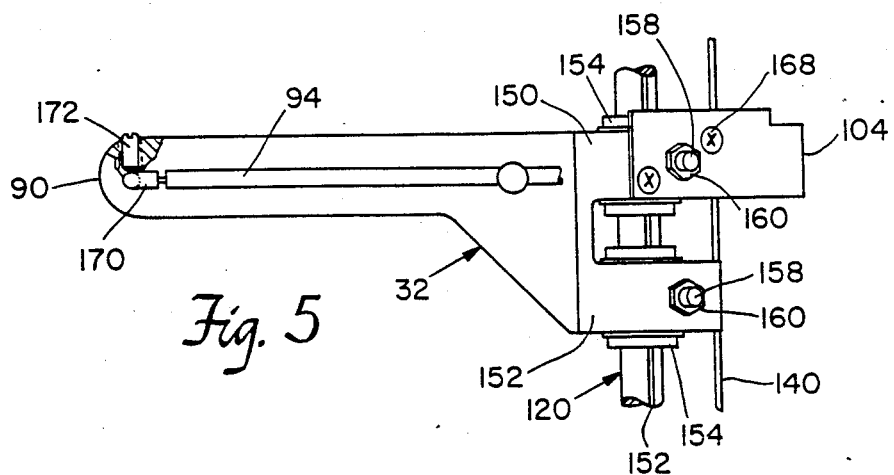
FIG. 5 is a top plan view of the probe arm assembly employed in the sample transfer system shown in FIGS. 3 and 4.
Figure 6:
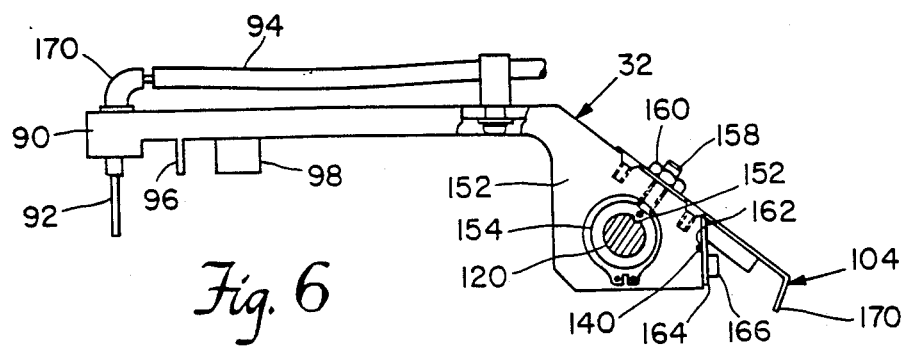
FIG. 6 is side elevational view of the probe arm assembly shown in FIG. 5.

Further details of the transport arm assembly 32 may be seen with reference to FIGS. 5 and 6. Probe arm 90 is of aluminum and has spaced bracket portions 150, 152, each of which receives a ball bushing 154 (Thompson Industries Super 6) that has a length of about two centimeters and receives one centimeter diameter shaft 120. Formed in shaft 120 is axially extending groove 152 and a series of bearing balls of each bushing 154 are urged into groove 156 by biasing members 158 that are secured by lock nuts 160.

Cable 140 is clamped in groove 162 in the rear surface of each bracket 150, 152 by clamp plate 164 and bolt 166. Sensor arm 104 is secured on bracket 150 by screws 168 and has sensor tip 170 that cooperates with sensors 106, 108, 110.

Carried on the forward portion of arm 90 is probe tube 92 (20 gauge stainless steel tube that has an inner diameter of about 0.6 millimeter and a length of about four centimeters) that is disposed in nylon collar 170 that is secured on arm 90 by spring loaded bushing 172. The tip of probe 92 projects about three centimeters below the top surface of arm 90. Also projecting down from arm 90 is sensor flag 96 that is located about 1.3 centimeters to the rear of the axis probe tube 92 and projects down about 1.5 centimeters; and a pair of valve actuator tabs 98 that are spaced about ½ centimeter apart and are about 2.1 centimeters from the axis of probe tube 92.

With reference to FIGS. 3 and 4, probe arm 32 is initially located in home position over wash station 20 (sensor 110) and contains diluent. Stepper motor 148 through cable 140 moves probe arm assembly 32 along shaft 120 to sample station (sensor 108), and metering pump 66 draws in 2.2 microliters of air, stepper motor 134 then rotates shaft 120 to pivot the probe arm assembly 32 over a 9° range to insert the tip of probe tube 92 into a sample cup 18, and then pump 66 draws in a programmed quantity of sample, the bubble of air separating sample from diluent. Probe arm 90 is then moved up by motor 134 and horizontally by motor 148 towards the fluidic modules 22. When the sensor flag 96 is sensed by sensor 102 of the desired first module (as indicated in FIGS. 7 and 8), controller 38 slows stepper motor 148 for 85 steps to move probe arm 32 to position the valve actuator members 98 over the valve actuator post 86. Stepper motor 134 then is operated for 26 steps to rotate shaft 120 and lower the valve actuator tabs 98 on either side of actuator post 86; stepper motor 148 is then operated for 100 steps to move probe arm 90 horizontally and position the probe tube 92 over the port of sample chamber 82, concurrently opening the valve 24. Motor 134 is then operated for 38 steps to lower the tip of probe tube 92 toward and into the port of chamber 82, and a specified quantity of sample (as determined by the controller 38) is flowed by metering pump 66 into the manifold sample chamber 82.

After dispensing the specified quantity of sample, system controller 38 operates stepper motor 134 to raise the probe arm 90 so that the probe tip of probe 92 clears the module port; probe arm 90 is then moved horizontally by motor 148 and cable drive 140 to close the valve; motor 134 then raises the probe arm so that the valve actuator members 98 clear the valve actuator post 86; and the probe arm 90 is moved horizontally by motor 148 and drive cable 140 to position the probe at the next fluidic module 22 for repetition of the dispensing cycle. For example, in a particular analytical sequence, at the glucose urea nitrogen module 22C, twelve microliters of sample are dispensed; at the ion selective electrode module 22B, eleven microliters of sample are then dispensed; and at the creatinine module 22A, eighteen microliters of sample are then dispensed.

After the dispensing cycle has been completed, the system controller 38 operates motor 148 to move the probe assembly 32 to the wash station 20 (sensor 110), then operates motor 134 to rotate shaft 120 and insert probe tube 92 in wash station 20 to remove residue from the outside of tube 92 and pump 66 is operated to discharge any remaining sample from the probe tube. The system fills the probe tube 92 with diluent from reservoir 30 in preparation for the next sample transfer sequence.

While a particular embodiment of the invention has been shown and described, various modifications thereof will be apparent to those skilled in the art, and therefor is not intended that the invention be limited to the disclosed embodiment, or to details thereof, and departures may be made therefrom within the spirit and scope of the invention.

What is claimed is:
1. An analysis system comprising
analysis station structure,
sample station structure spaced from said analysis station structure along a straight line path,
support shaft structure disposed along an axis parallel to said straight line path,
a transport carriage, probe structure mounted on said transport carriage, said transport carriage being mounted on said support shaft structure for movement along said support shaft structure and keyed thereto for pivoting movement in response to rotation of said support shaft structure,
first drive means including a drive motor and flexible cable structure coupled between said carriage and said drive motor for moving said transport carriage along said shaft structure to selectively position said probe structure at said sample and analysis stations,
second drive means for rotating said shaft structure for inserting said probe structure into and withdrawing said probe structure from chamber structure at said sample and analysis station structures, and
metering means coupled to said probe structure for flowing liquid into and discharging liquid from said probe structure.

2. The system of claim 1 wherein said transport carriage includes sensor means, and further including sensor structure at each of said stations for cooperation with said sensor means carried by said transport carriage.

3. The system of claim 1 wherein said shaft structure is cylindrical and includes an axially extending groove in its surface, and said transport carriage includes bearing structure for engagement with said groove to allow axial motion of said transport carriage along said shaft and pivoting movement of said transport carriage in response to rotational movement of said shaft.

4. An analysis system comprising
analysis stations structure,
sample station structure spaced from said analysis station structure along a straight line path,
support shaft structure disposed along an axis parallel to said straight line path,
a transport carriage, probe structure mounted on said transport carriage, said transport carriage being mounted on said support shaft structure for movement along said support shaft structure and keyed thereto for pivoting movement in response to rotation of said support shaft structure,
first drive means including a drive motor and flexible cable structure coupled between said carriage and said drive motor for moving said transport carriage along said shaft structure to selectively position said probe structure at said sample and analysis stations, said flexible cable structure including a drive sheave coupled to said drive motor, an idler sheave spaced from said drive sheave along a path parallel to said straight line path, and a flexible cable that is trained about said idler sheave, both ends of said flexible cable being connected to said drive sheave,
second drive means for rotating said shaft structure for inserting said probe structure into and withdrawing said probe structure from chamber structure at said sample and analysis station structures, and
metering means coupled to said probe structure for flowing liquid into and discharging liquid from said probe structure.

5. The system of claim 4 and further including biasing means for said idler sheave arranged to apply tension to said flexible cable.

6. The system of claim 5 wherein said transport carriage includes sensor means, and further including sensor structure at each of said stations for cooperation with said sensor means carried by said transport carriage.

7. A sample analysis system comprising
a plurality of flow network module structures, each said flow network module structure defining a contained array of flow channels and a plurality of valves for controlling liquid flow through the flow channel array, each said module structure being adapted to be connected to an external source for applying a pressure differential to the flow channel array to produce liquid flow within channels of said array and each said module structure having chamber structure connected to said flow channel array with port structure at an outer surface of said module structure, valve structure movable between a first position in which said port structure is closed and a second position in which said port structure is open,
a corresponding plurality of sensor modules,
liquid transfer structure comprising transport structure and probe structure carried on said transport structure, said liquid transfer structure being arranged for movement between a source of liquid to be analyzed and said plurality of flow network module structures and including actuator structure carried on said transport structure for moving said valve structure from its first position to its second position concurrently with the movement of the probe structure into alignment with the chamber port structure for delivery of a quantity of sample material to the sample chamber and subsequent flow through the flow network array for interaction with an auxiliary fluid and transfer to an associated sensor module under the influence of an external pressure source.

8. The system of claim 7 wherein the valve structure of each said module structure includes mechanical valve actuator structure for moving said valve structure from its said first position to its said second position, and said actuator structure includes mechanical valve actuator mechanism for mechanical engagement with respective said valve actuator structures of said module structures for moving the associated valve structure to open position as said probe structure is positioned in alignment with the chamber inlet port.

9. The system of claim 7 wherein each said flow network module structure includes a face plate member that has a firm and stable support surface, a flexible sheet member clamped in conforming and mating engagement to the firm and stable face plate surface, a flow channel network formed in said face plate member, valve land portions in one of said engaged surfaces that separates adjacent flow channel portions, and a plurality of valve actuators arranged to flex said sheet member between a first position in which the surface of said valve sheet member is in mating and sealing engagement with the surface of said face plate member so that the valve land portion blocks flow between adjacent channel portions, and a second position in which the sheet surface is spaced from the first position and allows liquid flow across the land surface between adjacent channel portions.

10. The system of claim 9 wherein each said sample chamber has a volume of about fifty microliters.

11. A sample analysis system comprising a plurality of flow network module structures are located along a straight line path,
each said flow network module structure defining a contained array of flow channels and a plurality of valves for controlling liquid flow through the flow channel array, each said module structure being adapted to be connected to an external source for applying a pressure differential to the flow channel array to produce liquid flow within channels of said array and each said module structure having chamber structure connected to said flow channel array with port structure at an outer surface of said module structure and valve structure movable between a first position in which said port structure is closed and a second position in which said port structure is open,
sample station structure spaced from said module structures along said straight line path,
support shaft structure disposed along an axis parallel to said straight line path,
said liquid transfer structure includes a transport carriage that is mounted on said shaft structure for movement along said shaft structure and keyed thereto for pivoting movement in response to rotation of said shaft structure, probe structure carried on said transport carriage,
first drive means including a drive motor and flexible cable structure coupled between said carriage and said drive motor for moving said transport carriage along said shaft to selectively position said probe structure at said sample and module structures,
second drive means for rotating said shaft structure for inserting said probe structure into and withdrawing said probe structure from chamber structures of said module structures, and
metering means coupled to said probe structure for flowing liquid into and discharging liquid from said probe structure.

12. The system of claim 11 wherein said transport carriage includes sensor means, and further including sensor structure at each of said module structures for cooperation with said sensor means carried by said transport carriage.

13. The system of claim 11 wherein said shaft structure is cylindrical and includes an axially extending groove in its surface, and said transport carriage includes bearing structure for engagement with said groove to allow axial motion of said transport carriage along said shaft structures and pivoting movement of said transport carriage in response to rotational movement of said shaft structures.

14. The system of claim 11 wherein said cable structure includes a drive sheave coupled to said drive motor, an idler sheave spaced from said drive sheave along a path parallel to said straight line path, and a flexible cable that is trained about said idler sheave, both ends of said flexible cable being connected to said drive sheave.

15. The system of claim 14 and further including biasing means for said idler sheave arranged to apply tension to said flexible cable.

16. The system of claim 15 wherein each said module structure sample chamber has a volume of about fifty microliters.

17. The system of claim 16 wherein the valve structure of each said module structure includes mechanical valve actuator structure for moving said valve structure from its said first position to its said second position, and said liquid transfer structure includes mechanical valve actuator mechanism for mechanical engagement with respective said valve actuator structures of said module structures for moving the associated valve structure to open position as said probe structure is positioned is alignment with the chamber inlet port.

18. The system of claim 17 wherein said transport carriage includes sensor means, and further including sensor structure at each of said stations for cooperation with said sensor means carried by said transport carriage.

* * * * *

REEXAMINATION CERTIFICATE (1496th)
United States Patent [19]
Geiselman

[11] B1 4,906,432
[45] Certificate Issued  Jun. 25, 1991

[54] LIQUID HANDLING

[75] Inventor: Theodore S. Geiselman, Groveland, Mass.

[73] Assignee: Fisher Scientific Company, Pittsburgh, Pa.

Reexamination Request:
No. 90/002,189, Nov. 1, 1990

Reexamination Certificate for:
Patent No.: 4,906,432
Issued: Mar. 6, 1990
Appl. No.: 74,942
Filed: Jul. 17, 1987

[51] Int. Cl.$^5$ .................................... G01N 35/06
[52] U.S. Cl. .................................. 422/63; 422/72; 422/100
[58] Field of Search ............... 422/63, 64, 65, 66, 422/67, 72, 73, 81, 100; 137/559, 597, 884; 251/331

[56] References Cited
U.S. PATENT DOCUMENTS
4,195,665  4/1980  Nolan ........................ 137/624.18
4,422,151  12/1983  Gilson ........................ 364/496
4,844,872  7/1989  Geiselman .................. 422/100

FOREIGN PATENT DOCUMENTS
0040186  4/1981  European Pat. Off. .

Primary Examiner—Robert J. Warden

[57] ABSTRACT

An analysis system includes analysis station structure, sample station structure spaced from the analysis station structure along a straight line path, support shaft structure disposed along an axis parallel to the straight line path, and a transport carriage with probe structure mounted on the carriage. The transport carriage is mounted on the support shaft structure for movement along that shaft and is keyed thereto for pivoting movement in response to rotation of the shaft. A first drive includes a drive motor and cable structure coupled between the carriage and the drive motor for moving the transport carriage along the shaft to selectively position the probe structure at the sample and analysis stations, and a second drive rotates the shaft for inserting the probe into and withdrawing the probe from chamber structure at the sample and analysis stations. Metering means coupled to the probe flows liquid into and discharges liquid from the probe.

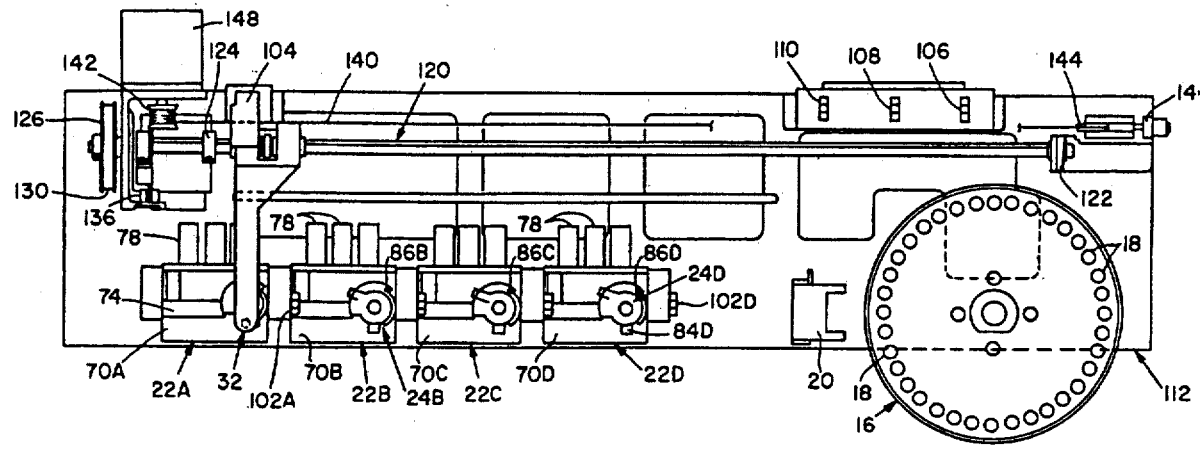

REEXAMINATION CERTIFICATE ISSUED UNDER 35 U.S.C. 307

NO AMENDMENTS HAVE BEEN MADE TO THE PATENT

AS A RESULT OF REEXAMINATION, IS HAS BEEN DETERMINED THAT:

The patentability of claims 1-18 is confirmed.

* * * * *